US009420977B2

(12) United States Patent
Crawford et al.

(10) Patent No.: US 9,420,977 B2
(45) Date of Patent: Aug. 23, 2016

(54) PORTABLE HEAD CT SCANNER

(71) Applicant: TRIBOGENICS, INC., Marina Del Rey, CA (US)

(72) Inventors: Carl Crawford, Glendale, WI (US); Dale Fox, Marina Del Rey, CA (US); Carlos Camara, Marina Del Rey, CA (US); Aldis Rauda, Marina Del Rey, CA (US)

(73) Assignee: Tribogenics, Inc., Los Angeles, CA (US)

( * ) Notice: Subject to any disclaimer, the term of this patent is extended or adjusted under 35 U.S.C. 154(b) by 169 days.

(21) Appl. No.: 14/219,846

(22) Filed: Mar. 19, 2014

(65) Prior Publication Data
US 2015/0265225 A1 Sep. 24, 2015

(51) Int. Cl.
*A61B 6/03* (2006.01)
*A61B 6/00* (2006.01)

(52) U.S. Cl.
CPC ............ *A61B 6/035* (2013.01); *A61B 6/032* (2013.01); *A61B 6/40* (2013.01); *A61B 6/4405* (2013.01); *A61B 6/4411* (2013.01)

(58) Field of Classification Search
CPC ...... A61B 6/032; A61B 6/035; A61B 6/4405; A61B 6/4411; A61B 6/4452; A61B 6/40; G01N 23/046
USPC ........................................ 378/4, 19, 196–198
See application file for complete search history.

(56) References Cited

U.S. PATENT DOCUMENTS

| 5,448,608 | A | * | 9/1995 | Swain | A61B 6/035 378/15 |
| 6,203,196 | B1 | | 3/2001 | Meyer et al. | |
| 6,940,941 | B2 | * | 9/2005 | Gregerson | A61B 6/032 250/363.05 |
| 7,001,045 | B2 | * | 2/2006 | Gregerson | A61B 6/035 362/253 |
| 7,175,347 | B2 | * | 2/2007 | Tybinkowski | A61B 6/032 378/196 |
| 7,338,207 | B2 | * | 3/2008 | Gregerson | A61B 6/032 378/17 |
| 7,393,138 | B2 | * | 7/2008 | Schindler | A61B 6/4488 378/15 |
| 8,118,488 | B2 | | 2/2012 | Gregerson | |

(Continued)

FOREIGN PATENT DOCUMENTS

EP 1511423 B1 8/2007
EP 1474040 B1 10/2007

(Continued)

OTHER PUBLICATIONS

J. R. Hird, C. G. Camara, and S. J. Putterman, "A triboelectric x-ray source," Applied Physics Letters 98, 133501 (2011).*

(Continued)

*Primary Examiner* — Allen C. Ho
(74) *Attorney, Agent, or Firm* — Klein, O'Neill & Singh, LLP

(57) ABSTRACT

A portable CT scanner may include a rotatable frame with separable portions. An x-ray source may be coupled to one portion of the rotatable frame, and an x-ray detector may be coupled to another portion of the rotatable frame. During storage and transportation, one portion of the rotatable frame may be housed in a first enclosure, and another portion of the rotatable frame may be housed in a second enclosure. When operation of the scanner is desired, the two enclosures may be connected, and/or the rotatable frame portions may be connected with the enclosures abutting one another, to allow for rotation of the rotatable frame about an aperture formed by the enclosures.

27 Claims, 10 Drawing Sheets

(56) References Cited

U.S. PATENT DOCUMENTS

| | | |
|---|---|---|
| 8,251,584 B2 | 8/2012 | Tybinkowski et al. |
| 8,379,797 B2 | 2/2013 | Abenaim et al. |
| 8,540,425 B2 | 9/2013 | Nielsen Groot |
| 8,662,750 B2 * | 3/2014 | Maschke ................ A61B 6/037 378/198 |
| 8,699,666 B2 * | 4/2014 | Putterman ................ H05G 2/00 378/119 |
| 8,870,456 B2 * | 10/2014 | Kim .................... A61B 6/4435 378/193 |
| 9,093,248 B2 * | 7/2015 | Putterman ............... H01J 35/16 |
| 9,125,613 B2 * | 9/2015 | Gregerson ........... A61B 6/4488 |
| 9,208,985 B2 * | 12/2015 | Camara .................. H01J 35/02 |
| 9,263,226 B2 * | 2/2016 | Zhao ...................... G01N 23/04 |
| 2004/0022350 A1 | 2/2004 | Gregerson et al. |
| 2005/0135560 A1 * | 6/2005 | Dafni .................. A61B 6/4405 378/101 |
| 2011/0280364 A1 | 11/2011 | Maschke |
| 2011/0316538 A1 | 12/2011 | Kim et al. |
| 2012/0256099 A1 | 10/2012 | Gregerson et al. |
| 2013/0202094 A1 | 8/2013 | Tybinkowski et al. |
| 2013/0243151 A1 | 9/2013 | Shih |
| 2013/0259202 A1 | 10/2013 | Sloutsky et al. |
| 2014/0003583 A1 | 1/2014 | Krupica et al. |

FOREIGN PATENT DOCUMENTS

| | | |
|---|---|---|
| WO | WO 03-070101 A1 | 8/2003 |
| WO | WO 2005/048843 A1 | 6/2005 |
| WO | WO 2005-058164 A1 | 6/2005 |

OTHER PUBLICATIONS

International Search Report on related PCT Application No. PCT/US2015/021549 from International Searching Authority (KIPO) dated Jun. 29, 2015.

Written Opinion on related PCT Application No. PCT/US2015/021549 from International Searching Authority (KIPO) dated Jun. 29, 2015.

* cited by examiner

PORTABLE HEAD CT SCANNER

BACKGROUND OF THE INVENTION

The present invention relates generally to x-ray imaging scanners, and more particularly to portable computer tomography (CT) scanners.

CT scanners are commonly used in healthcare applications, generally for diagnostic purposes. CT scanners usually include an x-ray source and an x-ray detector. The x-ray source and the x-ray detector are generally positioned on a rotatable frame such that the x-ray source and the x-ray detector are generally on, or centered on, opposite sides of an aperture. In use, a patient is positioned at least partially in the aperture, and rotation of the frame allows for multiple images of the portion of the patient within the aperture. In some instances, the patient may also be moved through the aperture, allowing for what may be termed a helical scan. In any event, image information, for example from measurement at varying angles, from the detector using measurements at varying angles is generally computationally operated on to form cross-sectional two-dimensional images of the patient.

In many instances CT scanners are limited to hospital or clinical settings. Although the diagnostic information provided by CT scanners may be useful outside of such settings, there are difficulties in use of CT scanners elsewhere. CT scanners are often relatively heavy, decreasing mobility of the scanners and some scanners may need to be mounted to solid foundations. CT scanners generally require a sufficiently large aperture to allow for passage of a human body, or significant parts thereof, resulting in a size requirement that may be unsuitable for use in, or transport through, compact spaces and for transport through conventional doors. Electrical power requirements for generating x-rays from an x-ray source are often significant, thereby often requiring access to utility line power sources. CT scanners may also require controlled environments for use or storage, for example with regard to temperature. In short, a variety of factors, for example weight, aperture size requirements, electrical power requirements, and storage and usage environment requirements impede the use of CT scanners outside of hospital and clinical settings.

BRIEF SUMMARY OF THE INVENTION

Aspects of the invention provide for a portable CT scanner and for various parts useful for a portable CT scanner. One aspect of the invention provides a portable scanning device for use in x-ray computed tomography (CT) scanning, comprising: a first enclosure containing a first portion of a rotatable frame, and an x-ray source fixedly coupled to the first portion of the rotatable frame; and a second enclosure containing a second portion of the rotatable frame, the second portion of the rotatable frame not coupled to the first portion of the rotatable frame when the first enclosure and the second enclosure are separated, and an x-ray detector fixedly coupled to the second portion of the rotatable frame.

In some aspects each of the first enclosure and the second enclosure include a wall defining a portion of an annular cavity, with the walls defining an annular cavity when the first enclosure and second enclosure are connected. In some aspects each of the first enclosure and the second enclosure have an arch-like shape. In some aspects the first enclosure and the second enclosure are couplable to form a structure with an aperture therethrough, with the rotatable frame rotatable, within the structure, about the aperture. In some aspects one of the first enclosure and the second enclosure includes a motor for rotating the rotatable frame. In some aspects one of the first enclosure and the second enclosure includes a battery for powering the motor. In some aspects the first portion of the rotatable frame includes a battery for powering the x-ray source and in some aspects, the detector. In some aspects the x-ray source is a tribocharging x-ray source. In some aspects the first portion of the rotatable frame and the second portion of the rotatable frame, when coupled, form an annular shape. In some aspects the first enclosure includes a pair of first enclosure openings normally covered by first enclosure opening covers, with the first portion of the rotatable frame rotatable so as to extend from either of the first enclosure openings. In some aspects the second enclosure includes a pair of second enclosure openings normally covered by second enclosure opening covers, with the second portion of the rotatable frame rotatable so as to extend from either of the second enclosure openings. In some aspects the first enclosure opening covers and the second enclosure opening covers are rotatable with the first portion of the rotatable frame and the second portion of the rotatable frame when the first enclosure and the second enclosure are connected. In some aspects the first enclosure opening covers are rotatable through the second enclosure openings when the first enclosure and the second enclosure are connected, and the second enclosure opening covers are rotatable through the first enclosure openings when the first enclosure and the second enclosure are connected. In some aspects the first enclosure opening covers are coupled to opposing ends of the first portion of the rotatable frame, and the second enclosure opening covers are coupled to opposing ends of the second portion of the rotatable frame. In some aspects the portable scanning device further comprises a first casing to cover the first enclosure and a second casing to cover the second enclosure, wherein the first casing is latchably connectable to the first enclosure and the second casing is latchably connectable to the second enclosure. In some aspects the first casing and the second casing each include a human holdable handle. In some aspects at least one of the first enclosure and the second enclosure includes a base for supporting the first enclosure, and the second enclosure when connected to the first enclosure, on a surface. In some aspects at least one of the first enclosure and the second enclosure has an upper surface abutments on opposing sides of a central portion providing a semi-circular cutout, with the upper surface being on an opposing side of at least one of the first and second enclosure than the base, with the upper surface and the base connected by side walls. In some aspects the first enclosure, the second enclosure, and contents of the first enclosure and the second enclosure, together weigh less than 54.43 kilograms or 120 pounds. In some aspects the rotatable frame is hand-rotatable.

In some aspects the invention provides a portable device for use in computed tomography (CT) scanning, comprising: a first enclosure containing a first portion of a rotatable frame, the first portion of the rotatable frame having a semicircular shape, with first opening covers mounted to ends of the semicircular shape, the first opening covers dimensioned so as to fill openings in the first enclosure through which the first portion of the rotatable frame may extend during rotation; a second enclosure containing a second portion of the rotatable frame, the second portion of the rotatable frame having a semicircular shape, with second opening covers mounted to ends of the semicircular shape, the second opening covers dimensioned so as to fill openings in the second enclosure through which the second portion of the rotatable frame may extend during rotation; a high energy radiation source fixedly coupled to the rotatable frame; and a high energy radiation detector fixedly coupled to the rotatable frame.

In some aspects the invention provides a portable device for use in computed tomography (CT) scanning, comprising: a first enclosure having a first pair of openings; a first portion of a rotatable frame within the first enclosure; a pair of first opening covers, each fixedly coupled to opposing ends of the first portion of the rotatable frame, and each dimensioned to substantially fill at least one of the openings in the first enclosure; a high energy radiation source fixedly coupled to the first portion of the rotatable frame; a second enclosure having a second pair of openings; a second portion of the rotatable frame within the second enclosure; a pair of second opening covers, each fixedly coupled to opposing ends of the second portion of the rotatable frame, and each dimensioned to substantially fill at least one of the openings in the second enclosure; and a high energy radiation detector coupled to the second portion of the rotatable frame.

In some aspects the invention provides a portable head CT scanner that is light enough and small enough to be transported in two or more containers, for example each about the size of large suitcase. In some aspects components are mounted on a rotatable frame that can be split into multiple sections, a plurality of which include components, and stored in the containers for transportation.

These and other aspects of the invention are more fully comprehended upon review of this disclosure.

DETAILED DESCRIPTION

Figure 1:
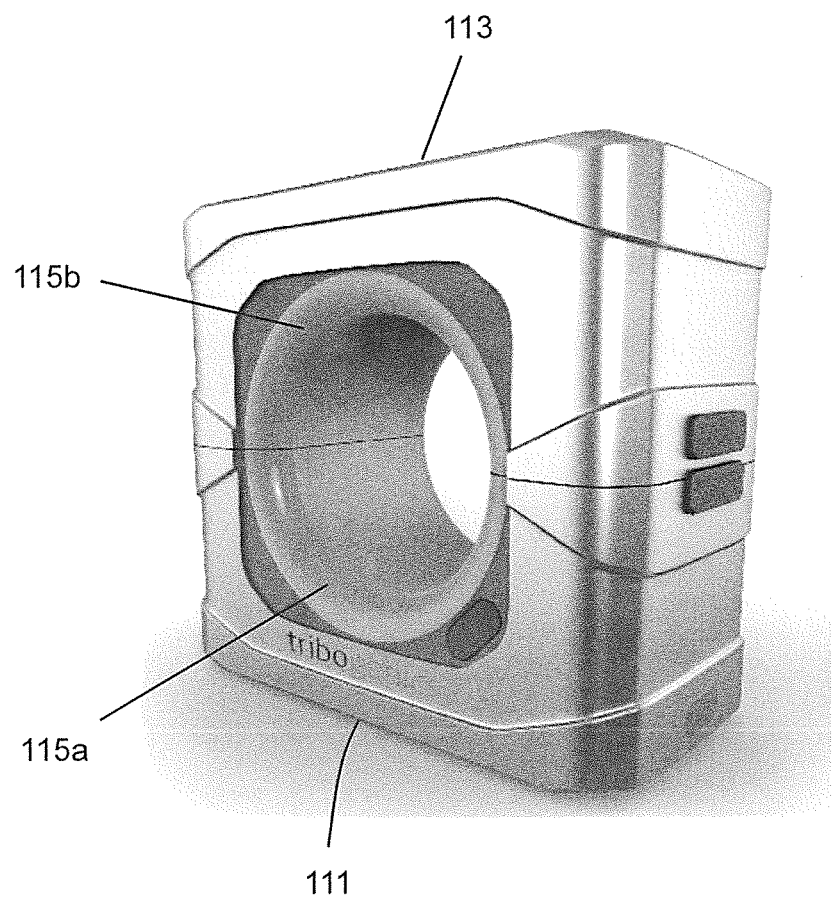
FIG. 1 is perspective view of a CT scanner in accordance with aspects of the invention.

FIG. 1 illustrates a CT scanner in accordance with aspects of the invention. The CT scanner of FIG. 1 includes a first enclosure 111 and a second enclosure 113. Although two enclosures are shown in FIG. 1, in various embodiments the CT scanner may be comprised of more than two enclosures. An aperture extends through the CT scanner, with the aperture defined by arches 115a and 115b in each of the first enclosure 111 and second enclosure 113. In operation, a rotatable frame including a high energy radiation source and a high energy radiation detector rotates about the aperture within the first enclosure 111 and second enclosure 113. In same embodiment the high energy radiation source is an x-ray source, and the high energy radiation detector is an x-ray detector. In some embodiments the high energy radiation source is a gamma ray source.

Figure 1A:
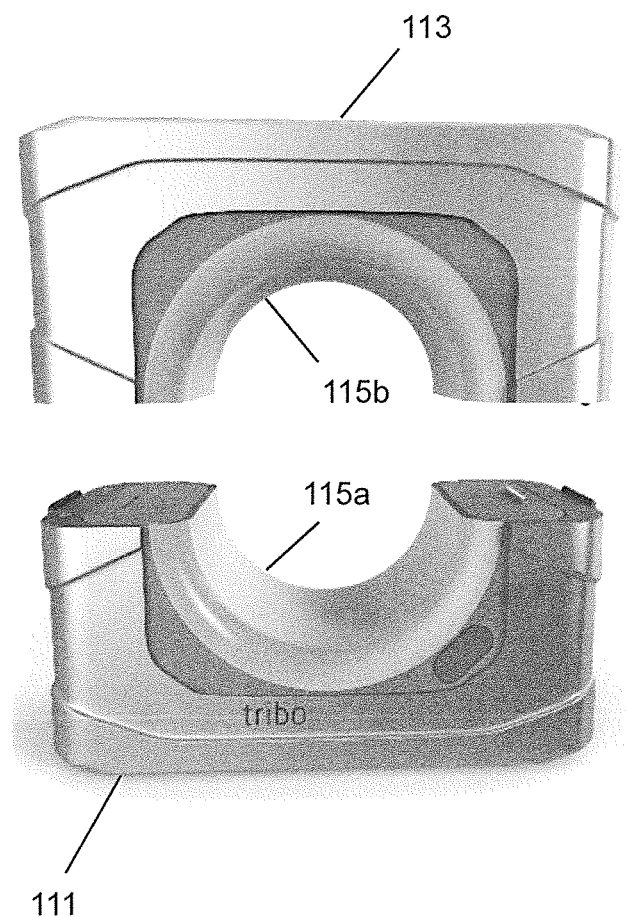
FIG. 1A illustrates a semi-perspective front view of the CT Scanner of FIG. 1, showing enclosures forming the CT Scanner separated and apart from each other.
Figure 2:
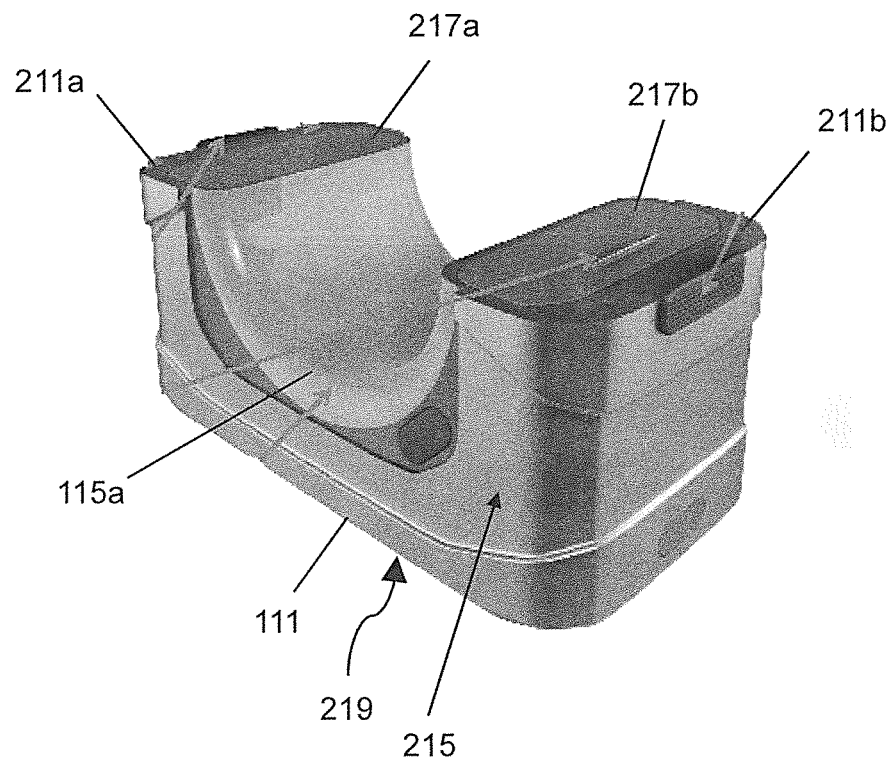
FIG. 2 is a perspective view of a first portion of the CT scanner of FIG. 1.

FIG. 1A shows the CT scanner of FIG. 1 with the first enclosure 111 and the second enclosure 113 separated from one another. As may be seen in FIG. 1A, each of the first enclosure 111 and the second enclosure 113 has arches 115a and 115b, semicircular in the embodiment of FIG. 1, which together define the aperture. FIG. 2 illustrates the first enclosure 111 of FIG. 1. An exterior view of the second enclosure 113 is, in various embodiments the same as or similar to that of the first enclosure 111. The first enclosure 111 may be considered to have an arch-like shape, with the arch-like shape generally vertically inverted. The first enclosure 111 has an upper surface featuring opposing side abutments 211a and 211b connected by an arch 115a defining a portion of the aperture. Sidewalls, shown generally as 215, extend downward to a substantially flat base 219. The substantially flat base 219 may support the first enclosure 111 on a surface, for example the ground in an outdoor setting, or a floor of some available structure.

Tops of the opposing side abutments 211a and 211b each include an enclosure opening cover 217a and 217b, respectively. The enclosure opening covers 217a and 217b conveniently cover openings in walls of the first enclosure 111 through which a portion of a rotatable frame within the first enclosure 111 may project during operation. In some embodiments the enclosure opening covers 217a and 217b cover the openings by being dimensioned so as to substantially fill the openings.

Figure 3:
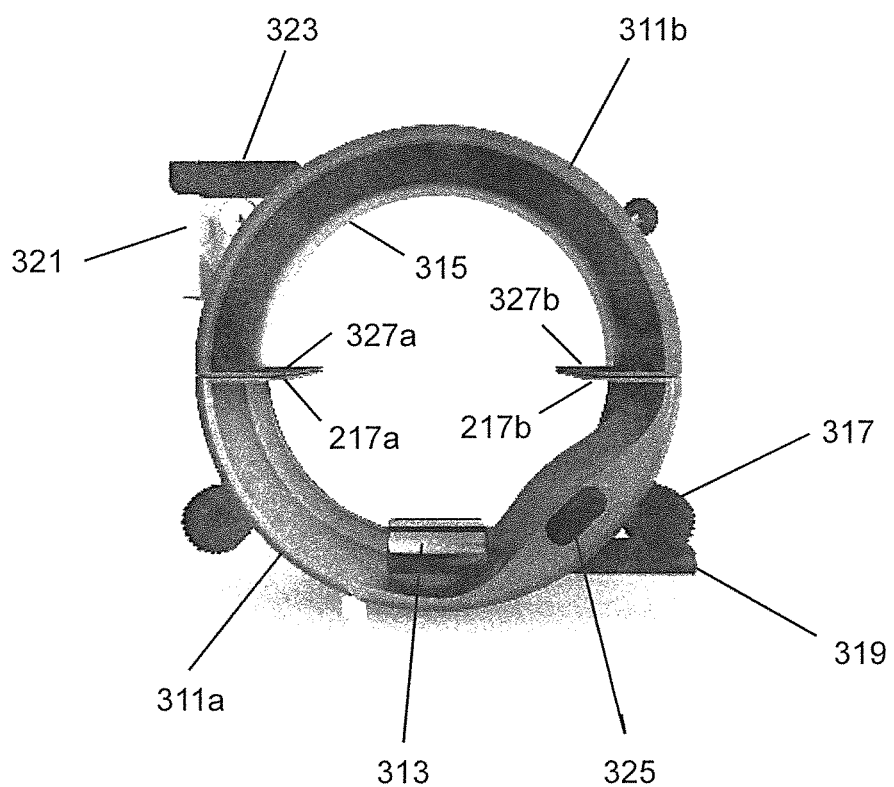
FIG. 3 is a front view of a portable frame and other components of a CT scanner in accordance with aspects of the invention.

FIG. 3 is a front view of a rotatable frame and other components of a CT scanner in accordance with aspects of the invention. In various embodiments the rotatable frame and other components may be part of the CT scanner of FIG. 1, and may be housed within the first enclosure 111 and the second enclosure 113 of the CT scanner of FIG. 1.

The rotatable fame is substantially annular, with the rotatable frame formed of a first portion 311a and a second portion 311b. The first portion 311a and the second portion 311b may be separated when the CT scanner is not in use, with for example the first portion 311a separately housed in the first enclosure 111 of the CT scanner of FIG. 1 and the second portion 311b separately housed in the second enclosure 113 of the CT scanner of FIG. 1. Both the first portion 311a and the second portion 311b are semi-annular in shape, so as to form, when combined as shown in FIG. 3, the substantially annular rotatable frame. In various embodiments an inner circumference of the rotatable frame is greater than circumference of an aperture of a CT scanner, of which the rotatable frame forms a part, to allow for rotation of the rotatable frame, and components mounted to the inner circumference, about the aperture.

In the embodiment of FIG. 3, an x-ray source 313 is fixedly coupled to the inner circumference of the first portion 311a of the rotatable frame, and an x-ray detector 315 is fixedly coupled to the inner circumference of the second portion 311b of the rotatable frame. The x-ray detector 315 is approximately centered on the inner circumference of the second portion 311b of the rotatable frame. The x-ray source 313 is, in some embodiments, an x-ray tube and a high voltage power supply. In other embodiments, the x-ray source 313 may be a tribocharging x-ray source, for example as discussed in U.S. patent application Ser. No. 13/523,551 (published as U.S. Patent Application Publication No. 2013/0336460), entitled "Friction Driven X-Ray Source," filed Jun. 14, 2012, the disclosure of which is incorporated by reference herein for all purposes. In many embodiments, a tribocharging x-ray source operates through application of frictional contact between tribocharging materials within a low fluid pressure environment, with the frictional contact preferably occurring proximate a target material such as a metal. In some embodiments the X-ray source is directly activated by mechanical motion that can be provided by any suitable source such as an electric motor or a hand crank.

As shown in FIG. 3, the first portion 311a of the rotatable frame and the second portion 311b of the rotatable frame are coupled by way of covers for enclosure openings, for example enclosure opening covers 217a and 217b for the first enclosure 111, as discussed with respect to FIG. 2, and corresponding enclosure opening covers 327a and 327b for the second enclosure 113. Use of the enclosure opening covers 217a and 217b in coupling the first portion 311a and the second portion 311b is convenient as doing so allows for coupling of the first portion 311a and the second portion 311b and operation of the CT scanner without exposing interior portions of the first enclosure 111 and the second enclosure 113 to the outside environment. Also the enclosure opening covers 217a, 217b, 327a, and 327b (and the enclosure openings covered by those covers) are sufficiently large that the first portion 311a and the second portion 311b of the rotatable frame, and items affixed thereto, may project through the enclosure openings during rotation of the rotatable frame.

Rotation of the rotatable frame about the aperture may be driven by one or more drive motors. In the embodiment at FIG. 3, a drive motor 317 is used to rotate the rotatable frame. The drive motor 317, generally with appropriate gearing as well, may be fixed in position within one of the first enclosure 111 and the second enclosure 113, about an exterior circumference of the rotatable frame. The drive motor 317 may be powered by a motor battery 319, which may be conveniently positioned in the same enclosure (e.g., the first enclosure 111 and/or the second enclosure 113) as the drive motor 317. In some embodiments, however, rotatable frame rotation may be hand-activated, for example by way of a handle, for example if a crank housing a spindle extending through a well of the enclosure, and gearing, or alternatively by direct access to the rotatable frame by way of an access way door in the enclosure.

A rotatable frame mounted battery 325 may be used to power the x-ray source 313. The rotatable frame mounted battery 325 may also power the x-ray detector 315, with for example the covers, or one pair of the covers, including electrical contacts to pass electrical power from one portion of the rotatable frame to the other. An electronics battery 323 may also be used to power CT scanner electronics 321, with the electronics battery 323 and the CT scanner electronics 321 mounted within one or the other of the first enclosure 111 and the second enclosure 113. In many embodiments the CT scanner electronics 321 may include control circuitry for controlling operation of the drive motor 317, x-ray source 313, and x-ray detector 315, and circuitry for receiving and/or processing x-ray detector information. In many embodiments the CT scanner electronics 321 includes wireless communication circuitry for communicating with the drive motor 317, x-ray source 313, and/or x-ray detector 315, and/or external devices in communication with the CT scanner, for example external command interfaces and/or image processing circuitry. In some embodiments the CT scanner electronics 321 may, in whole or in part, be instead or in addition be mounted on one or both parts of the rotatable frame.

Figure 4:
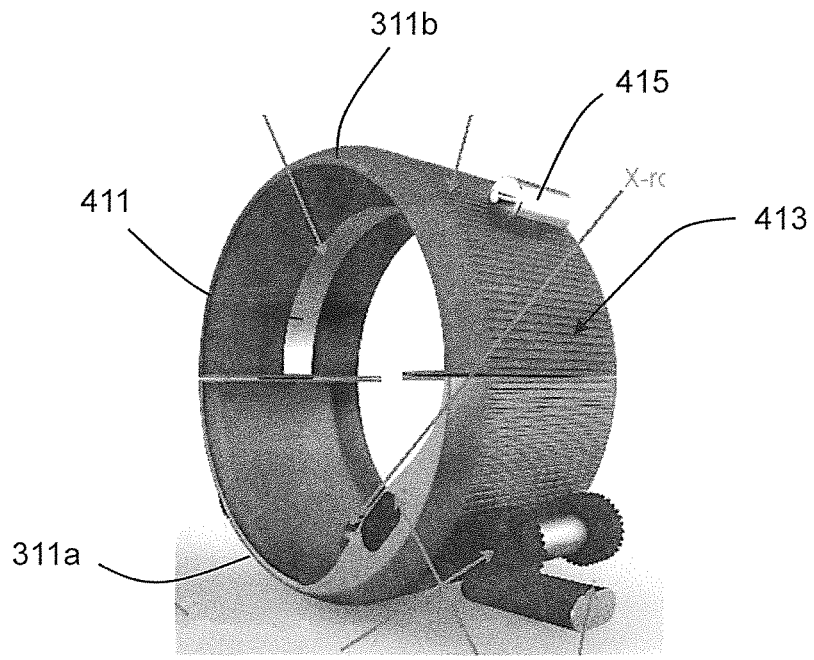
FIG. 4 is a perspective view of the rotatable frame and other components of FIG. 3.

FIG. 4 is a perspective view of the rotatable frame of FIG. 3, with the rotatable frame formed of the separable first portion 311a and second portion 311b. In the embodiment shown, an outer circumference 413 is geared, for example by way of ridges and valleys formed in the outer circumference. The ridges and valleys allow for greater correspondence between motor rotation and rotation of the rotatable frame, as well as serve to reduce slippage of position of the frame both during and between rotation.

The rotatable frame is shown in FIG. 4 with the x-ray detector cover removed. The x-ray detector cover is generally transparent to x-rays, with the x-ray detector cover normally covering an x-ray detector 411. The x-ray detector 411, in the embodiment of FIG. 4, substantially circumferentially extends across the second portion 311b of the rotatable frame. As such, the x-ray detector 411 may be considered as being centered approximately opposite the x-ray source.

Also visible in FIG. 4 is a roller 415. The roller is mounted within the enclosure about, and in most embodiments, in contact with the outer circumference of the second portion 311b of the rotatable frame. The roller 415 serves to maintain position of the rotatable frame during rotation of the rotatable frame.

Figure 5:
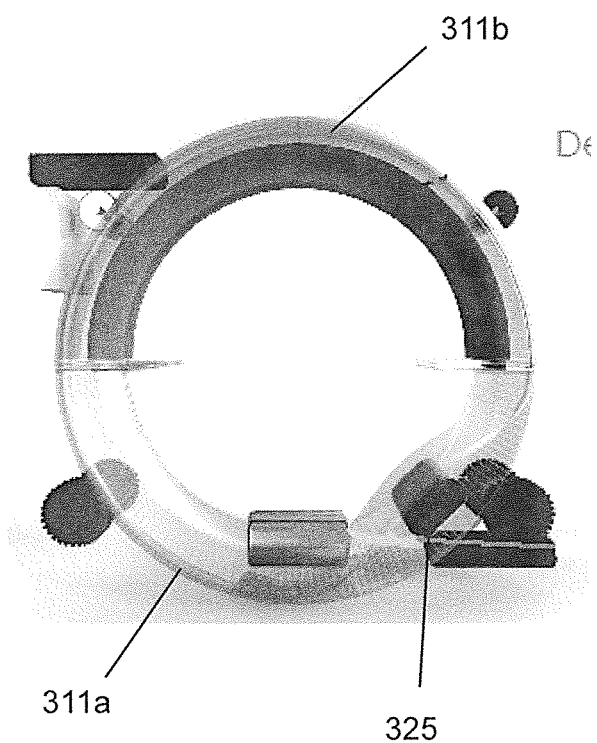
FIG. 5 is a front view of the rotatable frame and other components of a CT scanner, with a portion of the rotatable frame shown as transparent.

FIG. 5 is a front view of the rotatable frame and other components of a CT scanner, with a portion of the rotatable frame shown as transparent. As with other views, the rotatable frame includes a first portion 311a and a second portion 311b, with the first portion 311a and the second portion 311b separable. As may be seen in FIG. 5, part of the rotatable frame about the x-ray source is radially thickened, to allow for a cavity within the rotatable frame to hold the rotatable frame mounted battery 325.

Figure 6:
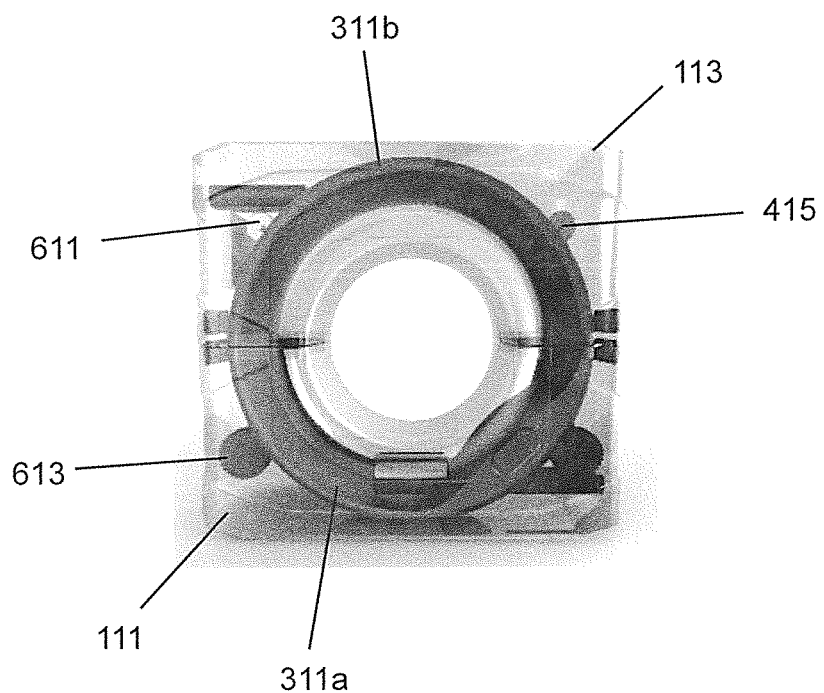
FIG. 6 is a front view of a CT scanner having features of the CT scanner of FIG. 1 and the rotatable frame and other components of FIG. 3, with portions of a housing of the CT scanner shown as transparent.

FIG. 6 is a front view of a CT scanner having features of the CT scanner of FIG. 1 and the rotatable frame and other components of FIG. 3, with portions of an enclosure, which may be formed of the first enclosure 111 and the second enclosure 113, of the CT scanner shown as transparent. With the first enclosure 111 and the second enclosure 113 shown as transparent, the rotatable frame, formed of the first portion 311a and the second portion 311b, may be seen within the first enclosure 111 and the second enclosure 113. Additionally the roller 415, serving to maintain rotatable position of the rotatable frame within the first enclosure 111 and the second enclosure 113, may also be seen, along with similar rollers 611 and 613, which serve similar functions.

Figure 7:
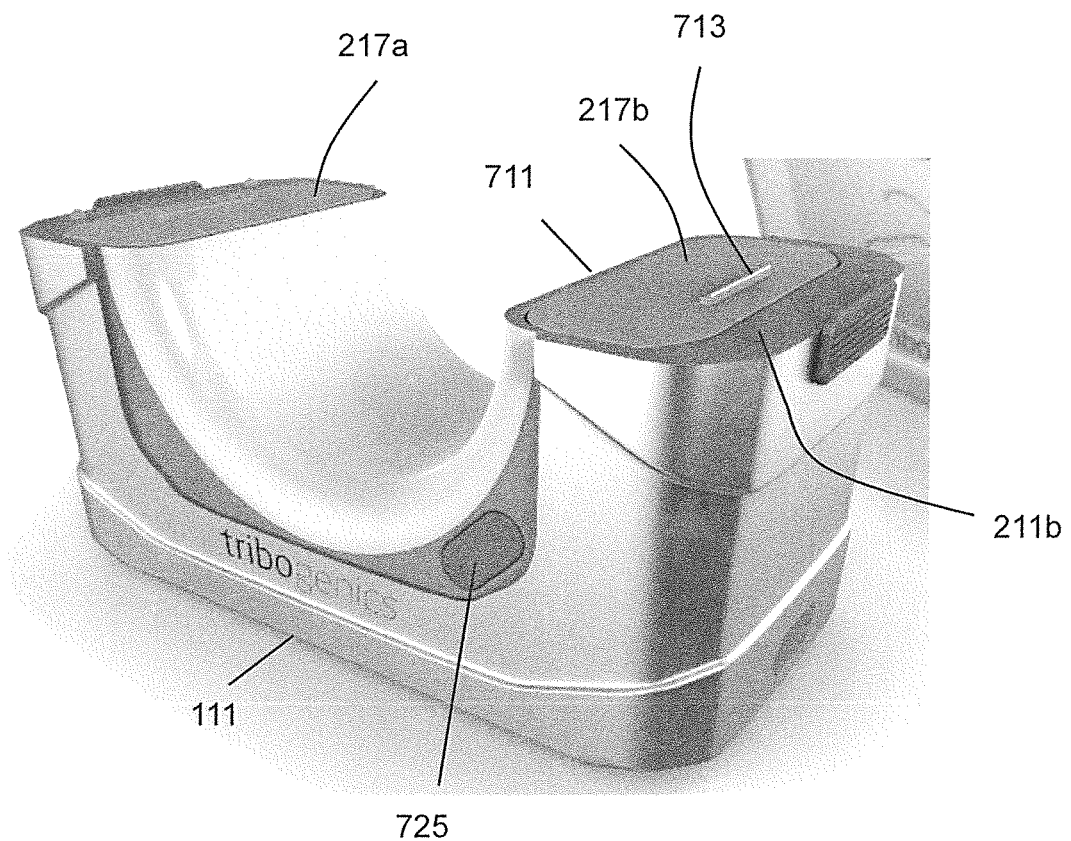
FIG. 7 is a further perspective view of the first enclosure of the CT scanner of FIG. 1.

FIG. 7 is a further perspective view of the first enclosure 111 of the CT scanner of FIG. 1. The view of FIG. 7, which is similar to that of FIG. 2, shows an access door 725, which provides access to the rotatable frame mounted battery 325 inserted into a cavity of the rotatable frame. Also visible in FIG. 7 are the enclosure opening covers 217a and 317b, with for example cover 217b flush with the top surface of abutment 211b. The enclosure opening covers 217a and 217b are inset from edges of the abutment 211a and 211b, with for example an inner edge portion 711 of the abutment 211b separating enclosure opening cover 217b from an edge of the cut-out portion of the upper surface of the first enclosure 111.

The enclosure opening covers 217a and 217b include a mechanical coupling feature, shown as item 713 for the enclosure opening cover 217b, to provide for coupling of the enclosure opening covers 217a and 217b with corresponding enclosure opening covers 327a and 327b of the second enclosure 113. The coupling feature 713 may, in some embodiments, include an electrical coupling feature, for example electrical contacts, for passing electrical power between the covers, provided for example by one portion of the rotatable frame and received by the other portion of the rotatable frame.

Figure 8:
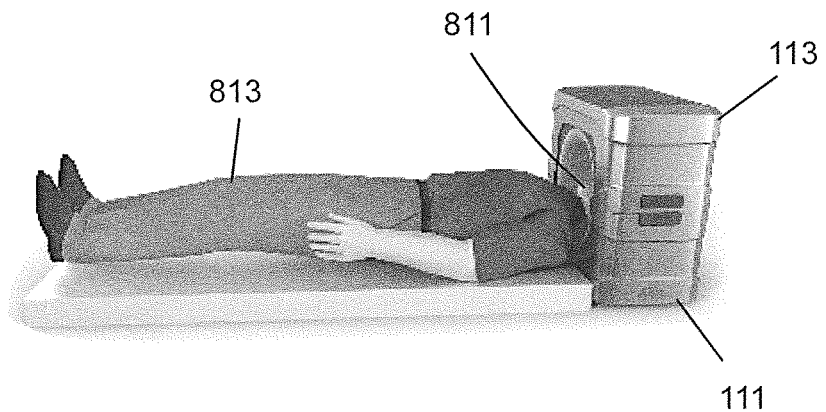
FIG. 8 is a perspective view of the CT scanner of FIG. 1 with a patient partially within an aperture of the CT scanner.

FIG. 8 is a perspective view of the CT scanner of FIG. 1, with a patient 813 partially within an aperture 811 of the CT scanner. A head of the patient 813 may rest on the cutout of the upper surface of the first enclosure 111, with a corresponding cutout of the second enclosure 113 above the patient's head. In the particular embodiment shown in FIG. 8, the aperture 811 is dimensioned so as to receive the patient's head, but is generally too small for receiving the patient's torso.

Figure 9:
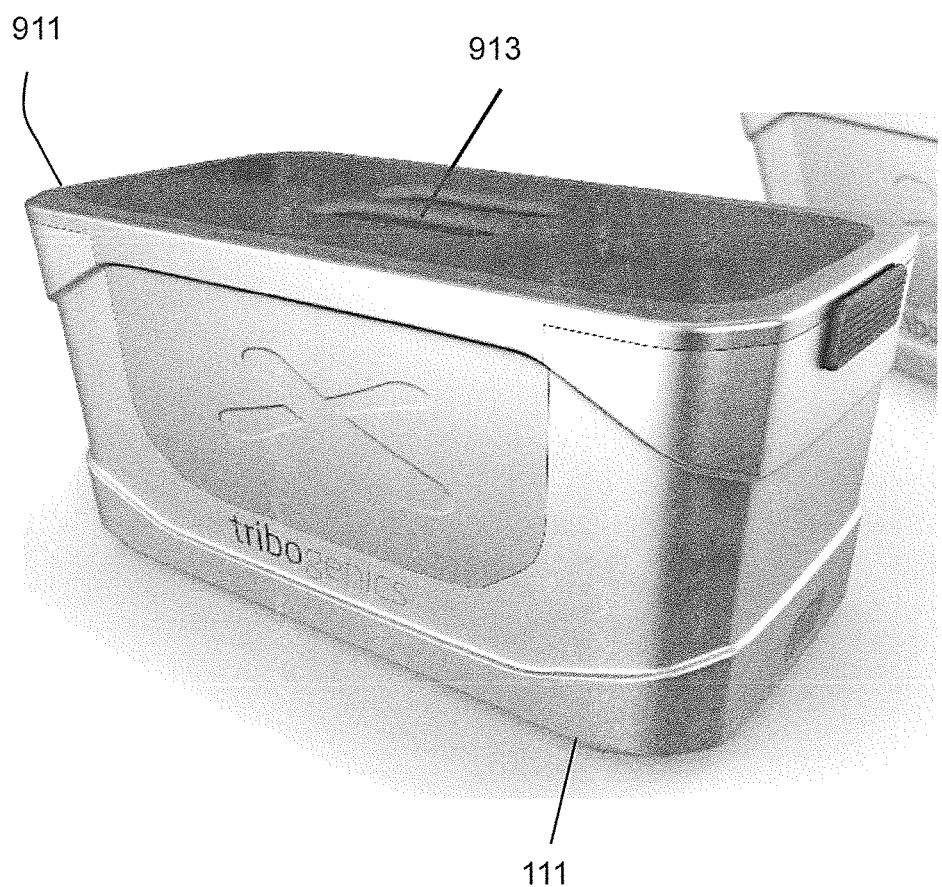
FIG. 9 is a perspective view of the first enclosure of FIG. 1 with a carrying case.

FIG. 9 is a perspective view of the first enclosure 111 of FIG. 1 with an optional carrying casing 911. The carrying casing 911 covers an upper portion of the first enclosure 111, and extends towards the base of the first enclosure 111. Another carrying casing, the same as or similar to the carrying casing 911 of FIG. 9, may be used for the second enclosure 113. A latching feature may be used to couple the carrying casing 911 to the first enclosure 111. With a latching feature used to couple the carrying casing 911 to the first enclosure 111, the carrying casing 911 may be considered latchably coupled to the first enclosure 111. In the embodiment of FIG. 9, the carrying casing includes a handle 913 for use in carrying the first enclosure 111. The handle 913 is preferably one that may be gripped by hand, with the handle 913 therefore being hand holdable.

Although the invention has been discussed with respect to various embodiments, it should be recognized that the invention comprises the novel and non-obvious claims supported by this disclosure.

What is claimed is:

1. A portable scanning device for use in computed tomography (CT) scanning, comprising:
    a first portion of a rotatable frame;
    a high energy radiation source fixedly coupled to the first portion of the rotatable frame;
    a first enclosure containing the first portion of the rotatable frame, and the high energy radiation source fixedly coupled to the first portion of the rotatable frame;
    a second portion of the rotatable frame;
    a high energy radiation detector fixedly coupled to the second portion of the rotatable frame;
    a second enclosure containing the second portion of the rotatable frame, the second portion of the rotatable frame not coupled to the first portion of the rotatable frame when the first enclosure and the second enclosure are separated, and the high energy radiation detector fixedly coupled to the second portion of the rotatable frame.

2. The portable scanning device of claim 1, wherein each of the first enclosure and the second enclosure includes a wall defining a portion of an annular cavity, with the walls defining an annular cavity when the first enclosure and the second enclosure are connected.

3. The portable scanning device of claim 1, wherein each of the first enclosure and the second enclosure has an arch-like shape.

4. The portable scanning device of claim 1, wherein the first enclosure and the second enclosure are couplable to form a structure with an aperture therethrough, with the rotatable frame rotatable, within the structure, about the aperture.

5. The portable scanning device of claim 1, wherein at least one of the first enclosure and the second enclosure includes a motor for rotating the rotatable frame.

6. The portable scanning device of claim 5, wherein the at least one of the first enclosure and the second enclosure includes a battery for powering the motor.

7. The portable scanning device of claim 1, wherein the first portion of the rotatable frame includes a battery for powering the high energy radiation source.

8. The portable scanning device of claim 1, wherein the first portion of the rotatable frame includes a battery for powering the high energy radiation source and the high energy radiation detector.

9. The portable scanning device of claim 1, wherein the high energy radiation source is an x-ray source.

10. The portable scanning device of claim 9, wherein the x-ray source is a tribocharging x-ray source.

11. The portable scanning device of claim 1, wherein the first portion of the rotatable frame and the second portion of the rotatable frame, when coupled, form an annular shape.

12. The portable scanning device of claim 1, wherein the first enclosure includes a pair of first enclosure openings, with the first portion of the rotatable frame rotatable so as to extend from either of the first enclosure openings.

13. The portable scanning device of claim 12, wherein the second enclosure includes a pair of second enclosure openings, with the second portion of the rotatable frame rotatable so as to extend from either of the second enclosure openings.

14. The portable scanning device of claim 13, further comprising first enclosure opening covers and second enclosure opening covers, and wherein the first enclosure openings are covered by the first enclosure opening covers when the first portion of the rotatable frame is within the first enclosure, and the second enclosure openings are covered by the second enclosure opening covers when the second portion of the rotatable frame is within the second enclosure.

15. The portable scanning device of claim 14, wherein the first enclosure opening covers and the second enclosure opening covers are rotatable with the first portion of the rotatable frame and the second portion of the rotatable frame when the first enclosure and the second enclosure are connected.

16. The portable scanning device of claim 15, wherein the first enclosure opening covers are rotatable through the second enclosure openings when the first enclosure and the second enclosure are connected, and the second enclosure opening covers are rotatable through the first enclosure openings when the first enclosure and the second enclosure are connected.

17. The portable scanning device of claim 16, wherein the first enclosure opening covers are coupled to opposing ends of the first portion of the rotatable frame, and the second enclosure opening covers are coupled to opposing ends of the second portion of the rotatable frame.

18. The portable scanning device of claim 1, further comprising a first case to substantially cover the first enclosure and a second casing to substantially cover the second enclosure, the first case latchably connectable to the first enclosure and the second casing latchably connectable to the second container.

19. The portable scanning device of claim 18, wherein the first casing and the second casing each include a human holdable handle.

20. The portable scanning device of claim 1, wherein at least one of the first enclosure and the second enclosure includes a base for supporting the first enclosure, and the second enclosure when connected to the first enclosure, on a surface.

21. The portable scanning device of claim 20, wherein the at least one of the first enclosure and the second enclosure has an upper surface including tops of abutments on opposing sides of a central portion providing a semi-circular cutout, with the upper surface being on an opposing side of the at least one of the first enclosure and the second enclosure than the base, with the upper surface and the base connected by side walls.

22. The portable scanning device of claim 1, wherein the first enclosure, the second enclosure, the first portion of the rotatable frame, the high energy radiation source, the second portion of the rotatable frame, and the high energy radiation detector, together weigh less than 120 pounds.

23. The portable scanning device of claim 1, wherein the rotatable frame is a hand-rotatable rotatable frame.

24. The portable scanning device of claim 23, wherein the rotatable frame is a crank hand-rotatable frame.

25. The portable scanning device of claim 24, wherein a crank for the crank hand-rotatable frame includes a spindle extending into a wall of one of the first and second enclosures.

26. A portable device for use in computed tomography (CT) scanning, comprising:
- a rotatable frame having a first portion and a second portion;
- a first enclosure containing the first portion of the rotatable frame, the first portion of the rotatable frame having a semicircular shape, with first opening covers mounted to ends of the semicircular shape, the first opening covers dimensioned so as to fill openings in the first enclosure through which the first portion of the rotatable frame may extend during rotation;
- a second enclosure containing the second portion of the rotatable frame, the second portion of the rotatable frame having a semicircular shape, with second opening covers mounted to ends of the semicircular shape, the second opening covers dimensioned so as to fill openings in the second enclosure through which the second portion of the rotatable frame may extend during rotation;
- a high energy radiation source fixedly coupled to the rotatable frame; and
- a high energy radiation detector fixedly coupled to the rotatable frame.

27. A portable device for use in computed tomography (CT) scanning, comprising:
- a first enclosure having a first pair of openings:
- a first portion of a rotatable frame within the first enclosure;
- a first pair of opening covers, each opening cover of the first pair of opening covers fixedly coupled to opposing ends of the first portion of the rotatable frame, and each opening cover of the first pair of opening covers dimensioned to substantially fill at least one of the first pair of openings in the first enclosure;
- a high energy radiation source fixedly coupled to the first portion of the rotatable frame;
- a second enclosure having a second pair of openings;
- a second portion of the rotatable frame within the second enclosure;
- a second pair of opening covers, each opening cover of the second pair of opening covers fixedly coupled to opposing ends of the second portion of the rotatable frame, and each opening cover of the first pair of opening covers dimensioned to substantially fill at least one of the second pair of openings in the second enclosure; and
- a high energy radiation detector coupled to the second portion of the rotatable frame.

* * * * *